(12) United States Patent
Fleischmann

(10) Patent No.: US 6,174,306 B1
(45) Date of Patent: Jan. 16, 2001

(54) DEVICE FOR VACUUM-SEALING AN INJURY

(76) Inventor: Wim Fleischmann, Nelkenweg 15, D-89182 Bernstadt (DE)

(*) Notice: Under 35 U.S.C. 154(b), the term of this patent shall be extended for 0 days.

(21) Appl. No.: 08/930,232
(22) PCT Filed: May 10, 1996
(86) PCT No.: PCT/DE96/00869
§ 371 Date: Sep. 12, 1997
§ 102(e) Date: Sep. 12, 1997
(87) PCT Pub. No.: WO96/35401
PCT Pub. Date: Nov. 14, 1996

(30) Foreign Application Priority Data

May 13, 1995 (DE) .............................. 195 17 699

(51) Int. Cl.⁷ .................................................. A61M 27/00
(52) U.S. Cl. ........................................... 604/543; 604/540
(58) Field of Search ...................... 604/35, 36, 38, 604/48, 73, 128, 133, 313, 315, 316, 540, 541, 543

(56) References Cited

U.S. PATENT DOCUMENTS

| 2,276,098 | * | 3/1942 | Saunders ............................ 604/315 |
| 3,779,243 | | 12/1973 | Tussey et al. ..................... 128/278 |
| 3,809,086 | | 5/1974 | Schachet et al. .................. 128/278 |
| 3,875,941 | * | 4/1975 | Adair .................................. 604/540 |
| 5,279,550 | * | 1/1994 | Habib et al. ....................... 604/38 |
| 5,636,643 | * | 6/1997 | Argenta et al. ................... 128/897 |

FOREIGN PATENT DOCUMENTS

93/09727  5/1993  (WO) .......................... A61B/19/00

* cited by examiner

Primary Examiner—Sharon Kennedy
Assistant Examiner—Cris L. Rodriguez
(74) Attorney, Agent, or Firm—Pendorf & Cutliff

(57) ABSTRACT

Described is a device for vacuum-sealing an injury (10), the injury being covered over by a film (14) to form an airtight seal. A drainage tube (18) laid under the film (14) is connected to a secretion-collection container (20). The container (20) is combined with a pump (24) so that the device can be used to provide ambulant aid.

2 Claims, 6 Drawing Sheets

DEVICE FOR VACUUM-SEALING AN INJURY

BACKGROUND OF THE INVENTION

1. Field of the Invention

The invention concerns a device for vacuum sealing an injury.

2. Description of the Related Art

For care of large surface area injuries with larger tissue defects it is known from WO93/09727 that the injury is covered over its surface with a film and closed off in an airtight manner. A drainage tube is introduced under the film and connected via a secretion-collecting container to a vacuum system. Thereby and under-pressurization or vacuum is produced in the wound area under the film, which beneficially influences the tissue regeneration and prevents the growth of bacteria. In larger injuries it is preferred that a porous foam insert be placed into the wound, into which the drainage tube is inserted, whereby the wound secretion can be siphoned or suctioned off over the overall wound surface area in a more even manner.

Until now a vacuum of approximately 80 kPa has been employed in this known device. In order to produce this vacuum, a vacuum pump is connected to the container for collection of the wound secretion, so that a suction effect of the pump continuously acts upon the container. Another possibility is comprised therein, that an evacuated container is employed which is changed out as soon as the vacuum in the container falls below a pre-determined value.

The research which underlies the present invention has shown, that this hitherto conventional vacuum is too high, in particular for chronic injuries. Pressures which are less than approximately ⅛ of the hitherto conventionally employed pressures, that is, approximately 10 kPa, appear to have a more beneficial effect on the healing process. The employment of continuously operating vacuum pumps is restricted to the patients at residence in a stationary clinical state. The employment of evacuated secretion collection containers is associated with significant problems at these low vacuums. Even small amounts of secretion, which are collected in the container, are sufficient to cause a substantial pressure drop in the container. Likewise, any breech or compromise of the seals, which in practice is difficult to avoid, results in an abrogation of the vacuum in the system.

DESCRIPTION OF THE RELATED ART

The invention is concerned with the problem of providing a device for vacuum sealing of a wound in which even a small under-pressurization in the range of 10 kPa or less can be maintained and which in particular can be employed ambulatory independent of a stationary clinical residence.

The essential concept of the invention is comprised therein, that the container for the collection of the wound secretion is associated with a pump, with which the under-pressurization or vacuum in the container and therewith the sealing of the wound is accomplished. The combination of the container and the pump makes the patient independent of the stationary vacuum system of the hospital, so that an ambulatory care of the acute and the chronically injured is possible. By means of the pump combined with a container, the under-pressurization of the container can at any time be maintained at a desired value. The patient can himself monitor the actual under-pressurization by means of a pressure gauge provided on the container and can as needed also correct the pressure to the desired pressure value.

The pump can be integrated completely into the container, so that the container and the pump are constructed as single use articles and after use can be collectively disposed of.

As an alternative possibility the pump can be releasably mounted on the container, which in certain cases simplifies the construction. Thereby there results a greater flexibility since the pump can be constructed or designed as a single use or as a multi-use article independent of whether the container itself is employed as a single or multi-use article. Finally, there is also the possibility that the pump is constructed as an independent component, which is coupled mechanically on the outside of the container and is in communication with the container via a connection hose.

Since the container with its pump is employed in an ambulatory manner and since the pump as a rule is employed only once or a few times, it is preferred to construct the pump in a simple, space saving and economical manner. These requirements are in harmony with the fact, that the pump need only be capable of providing small under-pressurizations, so that only minimal demands must be placed upon the capacity and quality of the pump. There can be employed, for example, a motorized pump, wherein simple and economical embodiments can be utilized, such as for example the so-called aquarium pumps.

Manual pumps can also be employed to advantage, for example, simple piston pumps. These manual pumps in addition have the advantage, that they are independent of an electrical power supply (current supply, battery).

In order that the vacuum in the container can be monitored and adjusted to the desired value, the container is equipped for example with a manometer. Here also, in consideration of the preferred single use construction and in consideration of the minimal precision requirements, a simple as possible and economical manometer is preferred. The manometer can for example be a spring bellows formed on the container which is drawn together or collapsed by the under-pressurization in the container and which correspondently expands upon the release of the vacuum.

In the case of a piston pump, the piston can be biased by a spring in the direction of its suction movement. Thereby an equilibrium condition is established between the spring force acting on the piston and the under-pressurization which acts in the opposite direction on the piston. If the under-pressurization relents, then the piston moves as a result of the spring force so far, until the equilibrium condition is again established. The under-pressurization is in this manner essentially made constant over the entire displacement space of the piston and can be pre-determined by selecting the spring force. A manual operation of the pump is only necessary at the time, when the piston has traveled back along its entire displacement space. The piston rod of the piston thereby can simultaneously serve as an indicator which makes a special manometer superfluous.

In a further embodiment, the container itself can fulfill the function of the pump. The container exhibits therefore a flexible outer wall, so that it can be compressed in the axial direction, in order to achieve an under-pressurization corresponding to its volumetric expansion. The axial volume increase can be achieved by a spring force, in which either the walls of the containers themselves are designed to function as spring bellows or a pressure spring is provided in the container. It is also possible to expand the container pneumatically. The force which expands the container volume, for example the spring force or, as the case may be, the pneumatic pressure, determine the under-pressurization produced in the container. Here also is produced a pre-determined vacuum corresponding to the mechanical spring force or, as the case may be, corresponding to the pneumatic pressure, which increases the container volume, and which is maintained constant by the cumulative expanding space of the container. A correcting of the under-pressurization is only necessary then when the container has traveled over its entire expansion displacement.

The film for covering and sealing the wound, the foam material insert, the drainage tube and the container with the pump are preferably provided as a complete set, so that the doctor has all the necessary components for care of the wound.

BRIEF DESCRIPTION OF THE DRAWING

In the following, the invention is further described by reference to the exemplary embodiments shown in the drawings. There are shown.

DETAILED DESCRIPTION OF THE INVENTION

Figure 1:
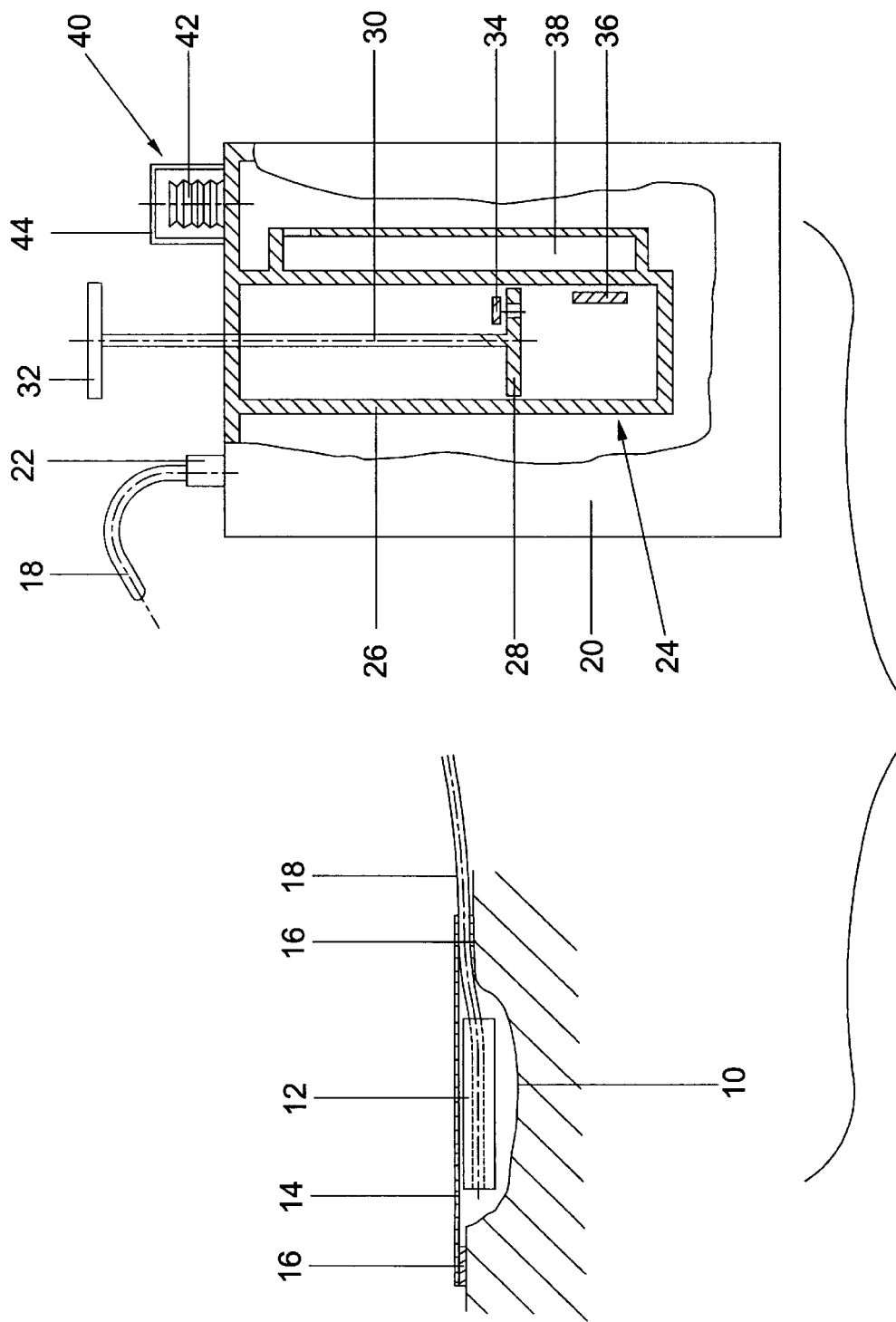
FIG. 1: schematic representation of a first embodiment of the device.

In FIG. 1, the entire device is schematically represented. In the wound 10 of the patient an insert 12 of an open pored form stable foam material is introduced. The wound 10 and the insert 12 are covered over with an airtight plastic foil or film. The film 14 attaches along the edges of the wound 10 and is brought into sealing engagement upon the skin of the patient around the wound circumference by a suitable adhesive material 16.

The distal end of the drainage tube 18 is inserted in the insert 12. The drainage tube 18 is provided with openings at its end situated in the insert 12, so that it is in communication with the wound through the pores of the insert 12.

The drainage tube 18 exits from under the film 14 sealed around it outer circumference.

At the proximal end of the drainage tube 18 a container 20 is attached. The container 20 is comprised of a plastic material and has the shape of a bottle or a pot.

In the exemplary embodiment according to FIG. 1, the container 20 is formed as a closed pot. At its upper lid surface a connection piece or attachment projection 22 with a hose "olive" is provided, upon which the drainage tube 18 is seated. In certain cases, the drainage tube 18 can also be provided as a unitary piece on the attachment projection 22. The drainage tube 18 is in communication with the internal space of the container 20 via the attachment projection 22.

Further, a pump 24 is provided on the inside space of the container 20. The pump 24 is comprised likewise of plastic material and is formed at the inner side of the upper lid surface of the container 20. The pump 24 is a simple piston pump with a cylinder 26, in which piston 28 in sealing engagement is displaceable. For moving the piston 28 there is provided a piston rod 30 connected to the piston 28, which extends through the upper lid surface of the container 20 and is provided with a handgrip 32. The piston 28 is provided with a one way valve 34 which opens during the pushing down of the piston 28. In the cylinder space below the piston 28 there is further provided in the wall of the cylinder 26 a one way valve 36, which opens inwards into the cylinder 26. Outside on the cylinder 26 the channel 38 is formed, which extends upwards from the one way valve 36 and which opens below the upper lid surface of the container 20 into the inside of the container.

On the upper lid surface of the container 20 there is provided a manometer 40. This is comprised of a spring bellows 42 of which the internal space is in communication with the inside of the container 20. The spring bellow 42 is enclosed with a cage 44 with axial sight windows, so that the axial expansion of the spring bellows 42 can be measured on a scale provided on the cage 44.

For care of the wound or injury, the insert 12 with the drainage tube 18 is laid in the wound 10 and covered with the foil or film 14 and sealed airtight. The container 20 is evacuated by means of the pump 24, preferably to a vacuum of approximately 10 kPa. The vacuum which exists at the time within the container 20 can be read at the manometer 40. The vacuum established in the container 20 extends through the drainage tube 18 and the porous foam material insert 12 and brings about an evacuation of the wound area under the film 14. The secretion extracted from the wound 10 is suctioned through the porous insert 12 and the drainage tube 18 into the container 20 and collected at the bottom of the container. If the patient determines by use of the manometer 40 that the prescribed vacuum in the container 20 is no longer maintained, so he can operate the pump 24 to return the vacuum again to the desired value. The container 20 with the integrated pump 24 is constructed in the present embodiment as a single use or one way article. When the container 20 is filled with wound secretion or when the wound treatment has concluded, the container 20 with the pump 24 and the collected secretions are disposed of.

Figure 2:
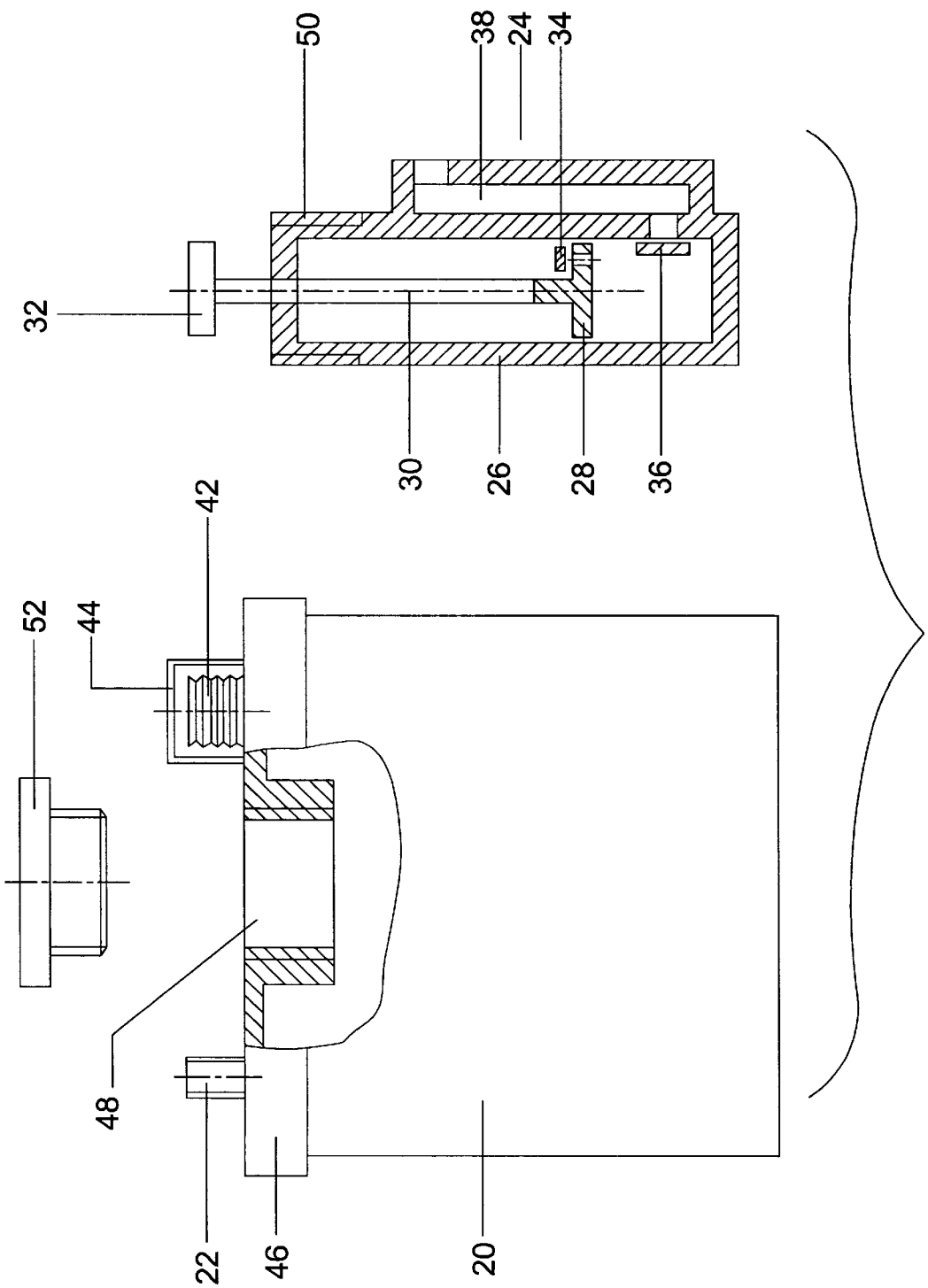
FIG. 2: the container and the pump in a second embodiment.

FIG. 2 shows an alternative second embodiment of the container 20 and the pump 24. In this embodiment, the container 20 is designed as a pot which opens from above, and which is sealed airtight by the attached lid 46. On the lid 46 there is formed an attachment projection 22 for the drainage tube 18. Likewise the spring bellows 42 and the cage 44 of the manometer 40 are formed on the lid 46.

The lid 46 is comprised of a through hole opening 48 with an internal threading. Through this opening 48 the pump 24 is introduced into the container 20 and with an outer threading 50 is sealingly screwed into the internal threading of the opening 48. The pump 24 is in all other respects constructed in the same manner as already described in regard to FIG. 1.

In place of the pump 24 a terminal closure or end cap 52 can be screwed into the opening 48, in order that the container 20 is securely closed.

The embodiment according to FIG. 2 is somewhat more expensive as compared to the embodiment according to FIG. 1. However, it has certain advantages over the embodiment as shown in FIG. 1. The container 20 can slightly conically constrict towards its floor, so that the container 20 after removal of the lid 46 can be stacked one within the other and can be stored and transported in a space saving manner. The pump 24 can be used one time or multiple times independently of the container.

The container 20 or as the case may be, the lid 46 can additionally be provided with a—not shown—attachment piece, with which the container 20 can be connected to an external stationary vacuum system. The device can thereby also be used in a stationary clinical environment, thereby the pump 24 is not required and the opening 48 can be closed with the end cap 52. The end cap 52 can be used for disposal of the container 20 with the collected secretion, in case the pump 24 is to be used multiple times.

Figure 3:
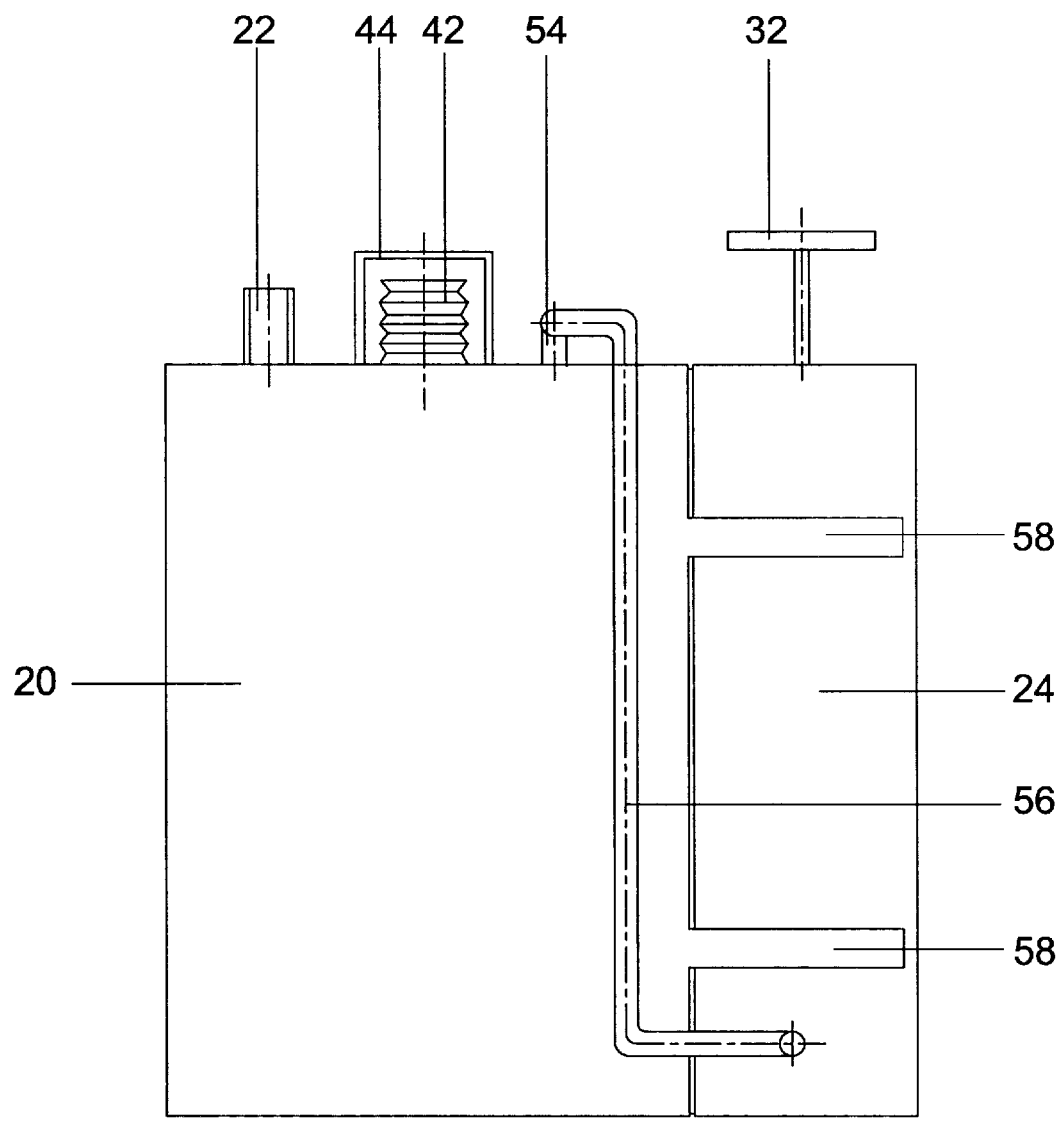
FIG. 3: the container and the pump in a third embodiment.

FIG. 3 shows a third embodiment of the container (20) with the pump 24.

In this embodiment, the container 20 is preferably constructed as a closed container. At the upper lid surface of the container 20 an attachment piece 54 is provided next to the connection piece 22 for the drainage tube 18 and the manometer 40, on which attachment piece 54 the pump 24 can be coupled by means of a connection tube 56. In order to unite the pump 24 with the container 20 the pump 24 is mechanically or form fittingly or by forcible attachment coupled to the outer side of the container 20. For this there can be used for example spring clamps 58 provided on the outer side of the container 20 in which the pump 24 is snap-fit, in order to be secured to the container 20 in a form fitting and a force fitting manner.

In the embodiment of FIG. 3 it is preferred that the pump 24 is intended for multiple uses. The container 20 is constructed particularly simply and accordingly suitable for a single use and for disposal with the collected secretion. At the attachment piece 54 a stationary vacuum system could be attached in the place of the pump 24 when the device is employed not for an ambulatory use, but rather, in a stationary clinical environment.

It is understood that also in the exemplary embodiment of FIG. 1 a supplemental attachment piece for the connection to the stationary vacuum system can be provided. Likewise, a known manometer type can be employed in the place of the spring bellows 42 type manometer 40.

Finally, it is also easy to see that in the place of the manual operated piston pump 24 other known types of pumps can be employed. In particular, simple electro-motor driven pumps can be employed. These pumps can also be integrated in the container 20 in accordance with the embodiment of FIG. 1, can be seatable in the container 20 according to the embodiment of FIG. 2, or can be coupleable to the outside of the container 20 according to the illustrative embodiment of FIG. 3.

Figure 4:
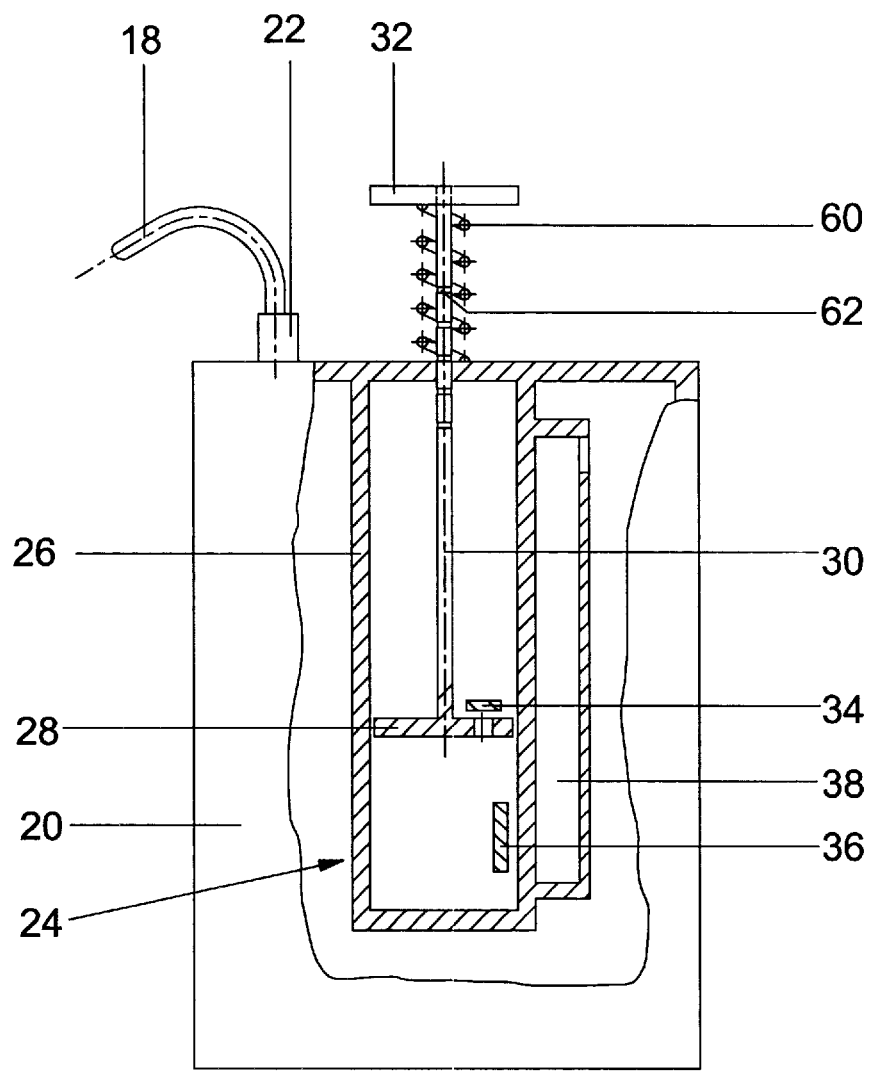
FIG. 4: the container and the pump in a fourth embodiment.

In FIG. 4 an fourth embodiment is shown, which is represented as a further evolvement out of the first embodiment.

Upon the piston rod 30 a spiral pressure spring 60 is seated between the lid surface of the container 20 and the hand grip 32 and which pulls the piston 28 in the cylinder 26 upwardly in the direction of suction. The spiral pressure spring 60 pulls the piston 28 so far upwardly, until on the inside of the container 20 a vacuum is produced which compensates the force of the spiral pressure spring 60. In the corresponding position of the piston 28 there is established an equilibrium condition between the force of the spiral pressure spring 60 and the vacuum and the container 20. If the vacuum in the system reduces on the drops due to loss of seal of the system or by the influx of secretion volumes, so then the spiral pressure spring 60 draws the piston 28 again further upwards until an equilibrium condition corresponding to the under-pressurization in the container 20 is again established. The pre-determined under-pressurization remains therewith for a long period of time and is maintained constant without any monitoring or correction being required. Only then when the piston 28 has traveled to its upper end position, a reduction of the vacuum can no longer be compensated for. Then the under-pressurization must again be established by manual operation of the pump. The piston 28 must again be brought to its lower end position, in order to reset its function for the automatic regulating of the vacuum.

The piston rod 30 can be provided with markations 62 which indicate that the vacuum must again be built up by pump operation. A supplemental manometer can be omitted in such an embodiment.

The handgrip 32 is preferably provided on the piston rod in a manner that it may be unscrewed, so that the spiral pressure spring 60 can be changed out. By the selection of a spiral pressure spring 60 with a specific spring constant the vacuum produced in the container 20 can be pre-determined.

In certain cases a spring may also be provided upon the piston rod 30 between the piston 28 and the outer lid surface of the container 20, which serves as an impact buffer, when the piston 28 is drawn upwards during operation of the pump.

The embodiment with the spiral pressure spring 60 can obviously be used in the pumps of the second and third embodiments according to FIG. 2 and 3.

Figure 5:
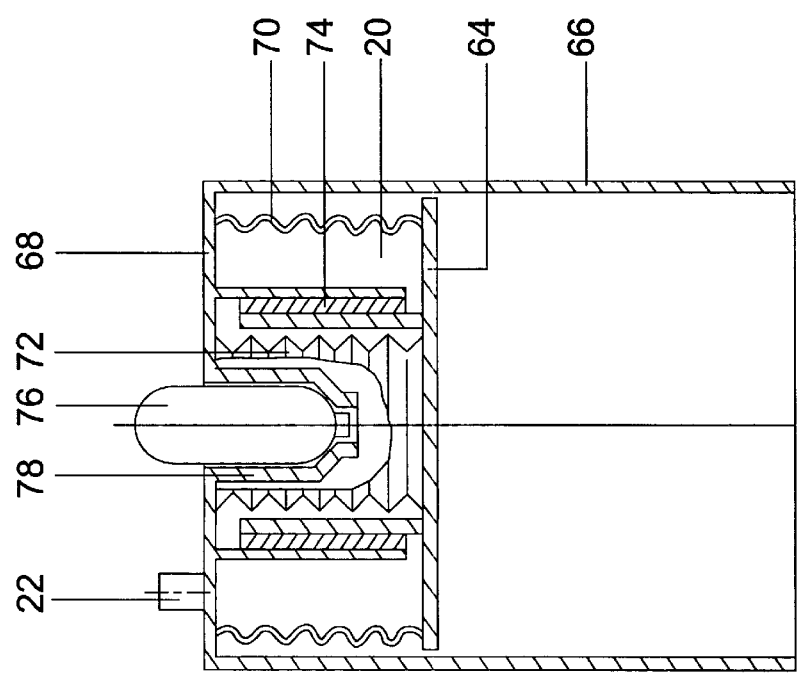
FIG. 5: the container in a fifth embodiment.

FIG. 5 shows a fifth embodiment, in which the container 20 simultaneously assumes the function of the pump.

The floor 64 of the container is guided axially, slidably, in the outer cylinder wall 66 of the container or as the case may be in a suitable, stably constructed cylindrical cage. The floor 64 is sealingly connected at its outer rim with the upper lid surface 68 of the container 20 by a flexible foil hose 70. The upper lid surface 68, the floor 64, and the foil hose 70 therewith enclose the inner space, of which the displacement is variable by the axial travel of the floor 64 and to which the drainage tube 18 can be connected via coupling piece 22.

Between the upper lid surface 68 of the container 20 and the floor 64 a closed cylindrical bellows 72 is seated centrally which at its outer circumference is guided by telescope tube 74 provided between the lid surface 68 and the floor 64. The bellows 73 can be placed under pressure pneumatically, so that it expands axially and the floor 64 is pushed axially downwards. The pneumatic pressure can for example be produced by a pump manually or electrically. A light, space saving and comfortable pneumatic operation of the bellows 72 is preferably achieved by a gas cartridge 76 which is seatable in an appropriate receptacle 78 at the upper lid surface 68 and is in communication with the inside of the bellows 72 via a valve.

In the fifth embodiment the device functions in the following manner. The floor 64 is completely pushed in, so that the inner volume of the container 20 is reduced. Then the drainage tube 18 is connected at the coupling piece 22. Now the gas cartridge 76 can be seated in the receptacle 78 so that gas under pressure flows into the bellows 72. The bellows 72 expands and displaces the floor 64 downwardly whereby the inner volume of the container 20 increases. The increase in the internal volume produces a vacuum in the container 20. An equilibrium condition forms, in which the vacuum in the container 20 compensates for the gas pressure in the bellows 72. If the under-pressurization decreases in the container 20 by lack of good seal of the system or by secretion influx, then the floor 64 is pushed further by the gas pressure in the bellows 72, so that the equilibrium pressure remains and is maintained constant.

If the floor 64 has traveled to its lower end position, then the gas cartridge 76 is removed and the container 20 can be emptied through the connection piece 22 by pressing in of the floor 64 or the container 20 can be disposed and replaced by a new container 20. After the emptying of the container or, as the case may be, the change out against a new container 20, the gas cylinder 76 is again seated and the suction process can again be resumed.

The floor 64 which travels in cylinder 66 serves at: the same time as an indicator therefore that the container 20 must be emptied or as the case may be changed out.

Figure 6:
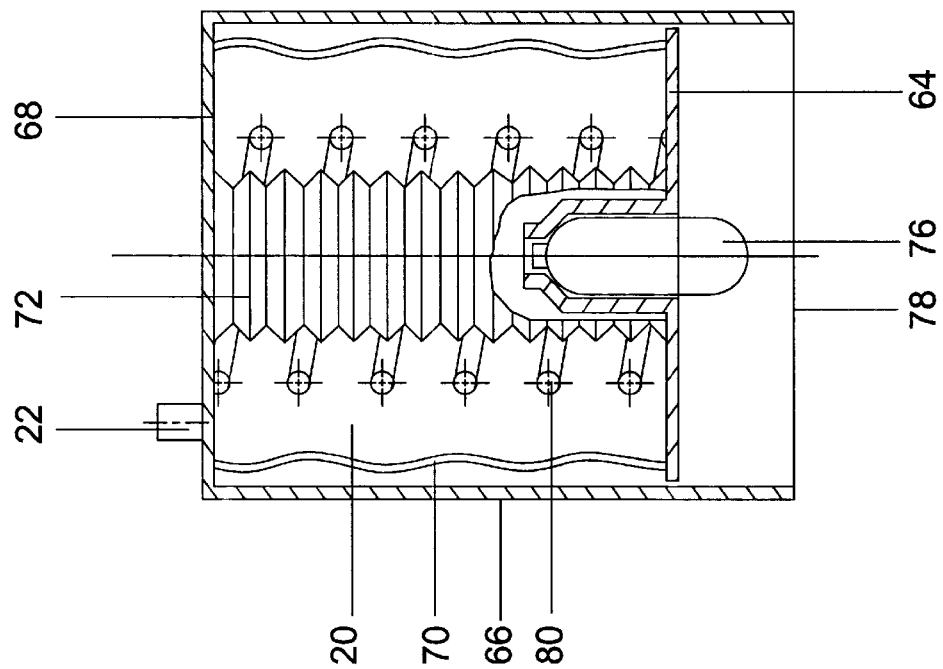
FIG. 6: the container in a sixth embodiment.

FIG. 6 shows a sixth embodiment which represents a variation from the embodiment according to FIG. 5.

In contrast to the illustrative embodiment according to FIG. 5, in this sixth embodiment a receptacle 78 for a gas cartridge 76 is provided in the floor 64 and in place of a telescopic tube a spiral spring 80 is seated between the floor 64 and the upper lid surface 68 in order to guide the bellows 72 against any sideways deviation. In FIG. 5 the container is represented at its beginning position for the beginning of the suction process, in which the floor 64 is completely pushed in while in FIG. 6 the end position is shown, in which the floor 64 is to be found at its lower end position and the suction process is ended. In other respects the embodiment according to FIG. 6 corresponds to the embodiment according to FIG. 5.

Figure 7:
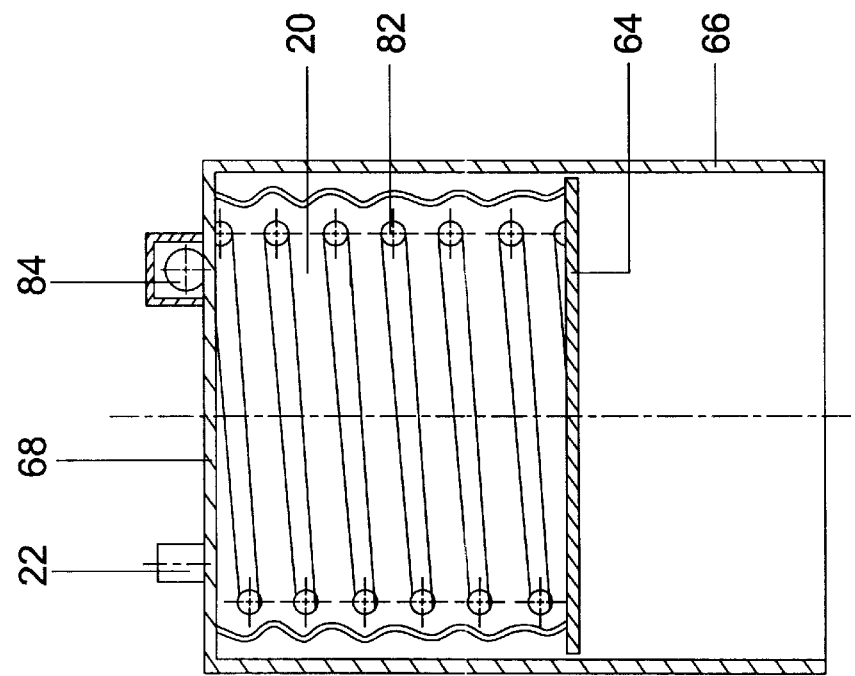
FIG. 7: the container in a seventh embodiment.

FIG. 7 shows a seventh embodiment which in large part corresponds to the embodiments of FIG. 5 and 6.

In contrast to the embodiments of FIG. 5 and 6, the force which pushes the floor 64 downwards in the cylinder wall 66 is not produced pneumatically, but rather by a spiral pressure spring 82 provided between the floor 64 and the upper lid surface 68.

The floor 64 is first pushed in against the force of the spiral pressure spring 82, in order to evacuate the internal volume of the container 20. After connection of the drainage tube 18 to the connection piece 22 the spiral pressure spring 82 pushes the floor downwards and enlarges thereby the internal volume of the container, until the equilibrium condition between the force of the spiral pressure spring 82 and the vacuum created in the internal volume of the container is achieved. The spiral pressure spring 82 pushes the floor 64 downwards, in order to maintain the equilibrium of the vacuum, when secretion or air leakage flow into the container 20.

In the lid surface 68 a one way valve 84 can be provided so that when, as a result of poor sealing, air flows into the container 20 so that the floor 64 travels completely downwards, the floor can be manually pressed in, without having to empty the secretion.

Figure 8:
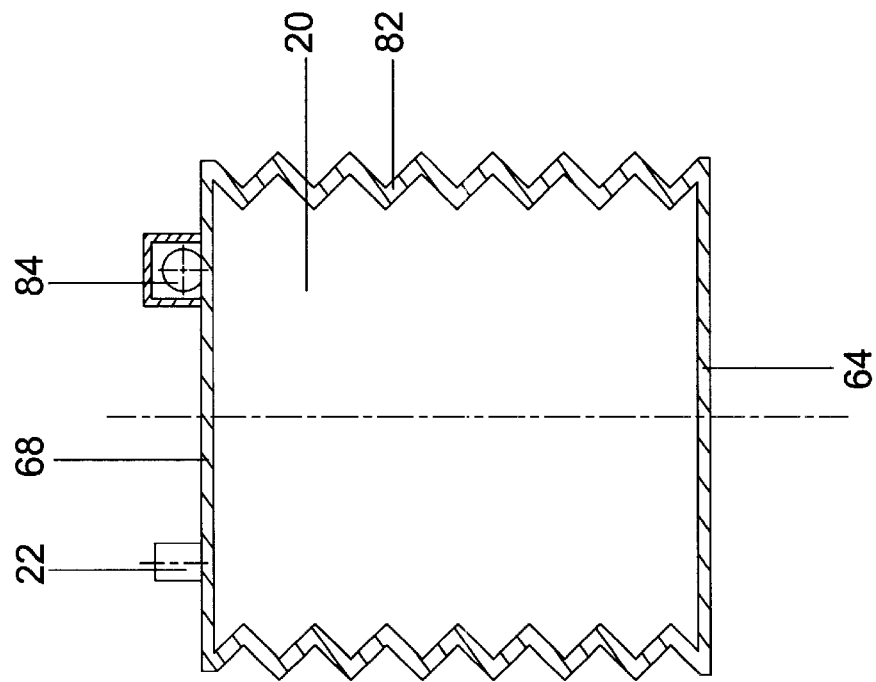
FIG. 8: the container in an eighth embodiment.

FIG. 8 shows a further embodiment, in which in place of the flexible foil hose 70 [sic] a form elastic spring bellows 86 sealingly connects the floor 64 with the upper lid surface 68. The spring bellows 86 axially guides the floor 64 and produces at the same time the spring force, which increases the inner volume of the container 20 and thereby produces the vacuum. Also here the equilibrium condition between the under-pressurization in the container 20 and the spring force of the spring bellows 86 leads to a constant vacuum over the cumulative displacement volume of the spring bellows 86.

What is claimed is:

1. Device for vacuum sealing a wound, comprising:
    a film adapted for covering and forming an airtight seal over a wound,
    a drainage tube having a proximal end and a distal end, of which the distal end is adapted to being introduced below the film in the wound for forming a vacuum between said film and said wound, and
    a container for collection of wound secretion connected to the proximal end of the drainage tube, and wherein said container (20) is constructed to have a variable internal volume,
    wherein the internal volume of the container (20) is defined by a floor (64), an upper lid (68) and a deformable wall (70, 86), wherein the container (20) comprises a floor (64) movable with respect to said lid, wherein the wall (70, 86) sealingly connects the floor (64) with the lid (68),
    wherein a bellows (72) is provided between the lid (68) and the floor (64) which bellows (72) is capable of being placed under pneumatic pressure to thereby increase the internal volume of, and create a vacuum in, said container (20), and wherein at least one of said lid (68) and said floor (64) is adapted for receiving a gas cartridge (76) such that said gas cartridge (76) is in communication with the inside of said bellows (72).

2. Device as in claim 1, wherein the position of the floor can be seen from the outside of the container and wherein the position of the floor indicates the pressure within the container.

* * * * *